(12) United States Patent
Hallundbæk et al.

(10) Patent No.: US 9,359,884 B2
(45) Date of Patent: Jun. 7, 2016

(54) POSITIONING TOOL (75) Inventors: Jørgen Hallundbæk, Græsted (DK); Mathias Francke, Virum (DK)

(73) Assignee: WELLTEC A/S, Allerød (DK)

(*) Notice: Subject to any disclaimer, the term of this patent is extended or adjusted under 35 U.S.C. 154(b) by 702 days.

(21) Appl. No.: 13/505,191

(22) PCT Filed: Oct. 29, 2010

(86) PCT No.: PCT/EP2010/066441
§ 371 (c)(1),
(2), (4) Date: Apr. 30, 2012

(87) PCT Pub. No.: WO2011/051429
PCT Pub. Date: May 5, 2011

(65) Prior Publication Data
US 2012/0217009 A1    Aug. 30, 2012

(30) Foreign Application Priority Data
Oct. 30, 2009   (EP) .................................... 09174665

(51) Int. Cl.
*E21B 47/092* (2012.01)
*E21B 47/09* (2012.01)
*G01N 27/72* (2006.01)
*G01V 11/00* (2006.01)

(52) U.S. Cl.
CPC ............ *E21B 47/0905* (2013.01); *G01N 27/72* (2013.01); *G01V 11/005* (2013.01)

(58) Field of Classification Search
CPC ......................... E21B 47/0905; G01V 11/005
USPC .............. 166/255.1, 255.2, 66, 66.5; 324/221
See application file for complete search history.

(56) References Cited

U.S. PATENT DOCUMENTS

| 2,717,039 | A | | 9/1955 | Gieske |
| 2,897,438 | A | * | 7/1959 | Fearon .......................... 324/221 |
| 2,967,994 | A | | 1/1961 | Peterson |
| 3,015,063 | A | * | 12/1961 | Ownby .......................... 324/221 |
| 3,570,594 | A | | 3/1971 | Hamilton |
| 3,843,923 | A | | 10/1974 | Devries et al. |
| 4,808,925 | A | * | 2/1989 | Baird .......................... 324/221 |

(Continued)

FOREIGN PATENT DOCUMENTS

| WO | WO 92/13174 | 8/1992 |
| WO | WO 2008139070 A1 * | 11/2008 |

OTHER PUBLICATIONS

Notification Concerning Transmittal of International Preliminary Report on Patentability, International Preliminary Report on Patentability and Written Opinion for corresponding PCT/EP2010/066441, issued May 1, 2012, 7 pages.
International Search Report for PCT/EP2010/066441 mailed Mar. 17, 2011.
Written Opinion of the International Searching Authority mailed Mar. 17, 2011.

*Primary Examiner* — Robert E Fuller
*Assistant Examiner* — David Carroll
(74) *Attorney, Agent, or Firm* — Nixon & Vanderhye P.C.

(57) ABSTRACT

A positioning tool for determining the position of the tool in a case downhole. The positioning tool utilizes a detecting unit which includes at least a first magnet and a first sensor in a first plane as well as a second sensor also arranged in the first plane. The first and second sensors are configured to detect changes in a magnetic field generated by the first magnet. The first sensor is arranged at a first distance from the first magnet and the second sensor is arranged at a second distance from the first sensor in the first plane.

20 Claims, 10 Drawing Sheets

(56) References Cited

U.S. PATENT DOCUMENTS

| | | | |
|---|---|---|---|
| 5,052,491 A * | 10/1991 | Harms et al. | 166/304 |
| 6,768,299 B2 | 7/2004 | Almaguer | |
| 7,990,138 B2 * | 8/2011 | Martin et al. | 324/221 |
| 8,471,556 B2 * | 6/2013 | Martin et al. | 324/221 |
| 2008/0150521 A1 | 6/2008 | Meeten et al. | |
| 2008/0236819 A1 * | 10/2008 | Foster et al. | 166/255.2 |
| 2009/0084546 A1 * | 4/2009 | Ekseth et al. | 166/255.1 |
| 2009/0166035 A1 | 7/2009 | Almaguer | |
| 2010/0045278 A1 * | 2/2010 | Martin et al. | 324/221 |

* cited by examiner

POSITIONING TOOL

This application is the U.S. national phase of International Application No. PCT/EP2010/066441 filed 29 Oct. 2010 which designated the U.S. and claims priority to EP 09174665.1 filed 30 Oct. 2009, the entire contents of each of which are hereby incorporated by reference.

TECHNICAL FIELD

The present invention relates to a positioning tool for determining the position of a tool in a casing downhole.

BACKGROUND

When running a tool in a casing downhole, it may often be desirable to know the specific position of the tool. Especially when running different types of inspection or logging tools, it may be very important to know the exact location of each observation made during the inspection or logging. For this and several other reasons, many attempts have been made to develop a device capable of determining the position of the tool when situated downhole.

A known device for determining the position of a tool downhole is called a "Casing collar locator". Typically, a locator comprises one or more magnets and one or more coils for measuring changes in the magnetic and electrical flux when passing a collar or casing features significant enough to cause a measurable change. The device is thus only able to determine the position of the tool collar by collar and not between two collars, and in order to measure differences in the flux, the device must be moved with considerable speed in the casing.

Another "Casing collar locator" comprises one or more flux gate magnetometers in the form of coils for measuring the remaining or naturally occurring magnetism in the casing collars. However, in order to determine the position of the tool between the collars, the wireline depth must be used.

As shown in U.S. Pat. No. 6,768,299, a "Casing collar locator" may also comprise one magnetometer for measuring changes in the strength of the magnetic field generated from a magnet. The "Casing collar locator" may also comprise more than one magnetometer to achieve different modes of detection so that one magnetometer detects collars and the other magnetometers detect the direction of the tool in order to control the direction of the drilling head of the tool.

DESCRIPTION OF THE INVENTION

It is an object of the present invention to wholly or partly overcome the above disadvantages and drawbacks of the prior art. More specifically, it is an object to provide an alternative positioning tool capable of determining an exact position of the tool with respect to a known reference point, e.g. the well head.

Thus, it is an object to provide a tool capable of determining the position even between two collars along the length of a casing.

The above objects, together with numerous other objects, advantages, and features, which will become evident from the below description, are accomplished by a solution in accordance with the present invention by a positioning tool for determining a position in a casing downhole, the positioning tool having a longitudinal tool axis and comprising:

a detecting unit comprising:
 a first magnet for generating a magnetic field,
 a first sensor for measuring the magnitude and/or direction of the magnetic field, arranged in a first plane and at a first distance from the first magnet, for detecting changes in the magnetic field, and
 a second sensor for measuring the magnitude and/or direction of the magnetic field, arranged in the same first plane and at a second distance from the first sensor along the axis, also for detecting changes in the magnetic field,
wherein the sensors detect changes in the magnitude and/or direction of the magnetic field, the magnet having a magnetic field source axis substantially transverse to the longitudinal tool axis.

When the tool has both a magnet and two sensors, the positioning of the tool is independent of the velocity of the tool. The measurements conducted by the sensors can be processed into a fairly accurate estimate of the velocity of the tool and thereby a fairly accurate estimate of the position. Therefore, no additional tool is necessary to determine the position, and the position can be determined within two casing collars as well.

When the tool has two sensors positioned at a distance from each other, the measurements of the first sensor can be compared with the measurements of the second sensor, which leads to a more precise estimate of the present position of the tool, and the following operation depending on the position can thereby be determined more accurately.

The positioning tool may further comprise a second magnet, the first sensor being positioned in a first angle in relation to a longitudinal extension of the first magnet, and the second sensor having the first distance and angle in relation to a longitudinal extension of the second magnet.

In one embodiment, the sensors may be positioned at the same distance from the magnet.

These sensors may be anisotropic magnetoresistive sensors. By using anisotropic magnetoresistive sensors, the measurements of the sensors may be independent of the velocity of the tool.

The positioning tool may further comprise a second magnet, the second sensor being arranged in a position in relation to the second magnet, which position is the same as the position in which the first sensor is arranged in relation to the first magnet, as if the first sensor and magnet had been parallelly displaced, and the magnet may be arranged in the same first plane as the first and second sensors. By arranging the sensors in the same plane, a more precise position of the tool may be obtained.

Moreover, the first distance may be equal to the second distance.

Furthermore, the first and second sensors may be arranged on one side of the magnet and a plurality of sensors may be arranged on the other side in the first plane.

The magnet may be arranged on one side of a plate, and an additional magnet may be arranged on the other side of the plate so that two repelling poles of the magnets are facing one another. The plate may be made of a non-conductive or non-magnetic material, such as porcelain, ceramic, mica, glass, plastics, or a combination thereof.

The tool may comprise a plurality of magnets, each of which is arranged outside a sensor so that the first magnet is arranged outside the first sensor, and the second magnet is arranged outside the second sensor.

Furthermore, the at least one magnet may be a permanent magnet or an electromagnet.

Each sensor may measure the magnitude and/or direction of the magnetic field or the field vector, i.e. the strength and direction of the field.

The tool may have a cylindrical shape with a wall, and the detecting unit may be arranged inside the tool and surrounded by the wall.

The magnet may have a rectangular shape or a cylindrical shape.

The distance between two sensors may be between 5 and 150 mm, preferably between 5 and 100 mm, more preferably between 10 and 50 mm, and even more preferably between 10 and 30 mm.

Furthermore, the positioning tool may comprise a second detecting unit according to the above.

In addition, the distance between the detecting units in the tool may be between 100 mm and 10000 mm, preferably between 1000 mm and 5000 mm.

The invention also relates to a detecting unit as described above.

Moreover, the invention relates to a method for determining a position of a tool based on the measurements obtained from the positioning tool, comprising the steps of:
 measuring the magnitude and/or direction of a magnetic field by means of the first sensor several times over a time period,
 measuring the magnitude and/or direction of the magnetic field by means of the second sensor, and
 comparing the measurements from the first sensor with the measurements from the second sensor in order to calculate a velocity of the tool.

Moreover, the invention relates to a method as described above, wherein the steps of measuring the magnitude and/or direction of the magnetic field are performed several times over a time period, and wherein the step of comparing the measurements from the sensor is performed after this time period.

The tool may be moving during the measurements.

Furthermore, the invention relates to the use of the positioning tool as described above.

Moreover, the invention relates to a positioning system comprising the positioning tool and a calculation unit for processing magnetic field data measured by the sensors.

Finally, the invention relates to a downhole system comprising the positioning tool and a driving tool, such as a downhole tractor.

BRIEF DESCRIPTION OF THE DRAWINGS

The invention and its many advantages will be described in more detail below with reference to the accompanying schematic drawings, which for the purpose of illustration show some non-limiting embodiments and in which.

All these figures are highly schematic and not necessarily to scale, and they show only those parts which are necessary in order to elucidate the invention, other parts being omitted or merely suggested.

DETAILED DESCRIPTION OF THE INVENTION

The present invention relates to a positioning tool 1 for determining the position of a tool downhole before performing an operation downhole or for locating the position of a valve, an annular barrier, a sleeve, a patch, a leak in the casing, or any other feature resulting in a significant change in a magnetic field.

The positioning tool 1 may also advantageously be used for detecting a leak or a valve, since both a valve and a leak result in significant change in the magnetic field, and at the same time estimate the position of the leak or the valve. If the feature to be located downhole does not result in a significant change in the magnetic field or if further information regarding the condition of e.g. the valve is needed, the positioning tool 1 can be used in connection with an inspection tool or another logging tool. If the feature to be located does result in a significant change, the positioning tool 1 can also be used in connection with a drilling tool, a setting tool for setting a plug, a tool for inserting a liner or a patch, or a similar type of downhole tool. The downhole tools may also be connected with the positioning tool 1 if these tools need a position downhole to perform the specific operation in the well, such as drilling of a sidetrack.

Figure 1:
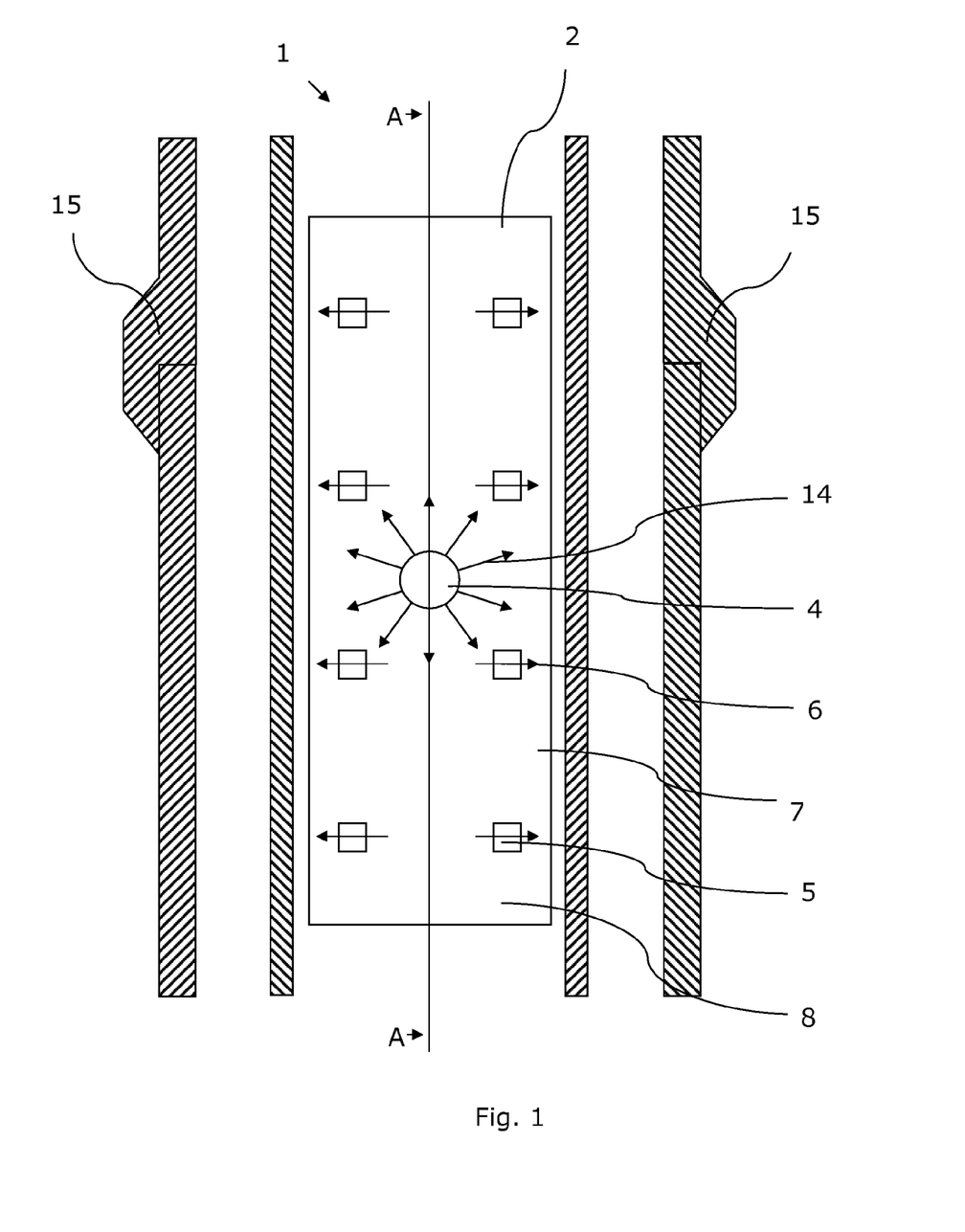
FIG. 1 shows a cross-sectional view of the positioning tool according to the invention.

A positioning tool 1 comprises a detection unit 2, as shown in FIG. 1. The detection unit 2 comprises a magnet 4 and eight sensors 5, 6. These sensors 5, 6 are positioned so that four sensors are positioned on each side of the magnet 4. The sensors 5, 6 are arranged with an axial distance $d_2$ from each other and in the same plane 7 as on a plate 8. The sensors 5, 6 are arranged at a first distance $d_1$ to the magnet 4 which is positioned on the same plate 8. In FIG. 1, the plate 8 is a circuit board.

The positioning tool 1 has a substantially cylindrical shape, and the detecting unit 2 is arranged in its centre, extending along the length the tool. The plate 8 is fastened to the wall of the tool 1. When the tool 1 moves down the casing 3, the magnetic field changes depending on the surroundings, and the sensors 5, 6 detect the direction θ of the magnetic field lines when the tool moves. By performing substantially continuous measurements of the direction and/or magnitude, small variations are measured while the tool 1 passes the part of the casing 3 between two collars or joints. The small variations may be caused by the fact that the casing 3 is slightly inaccurate in thickness throughout its entire length or that the casing may have a varying density. The sensors are also able to detect if no changes occur in the magnetic field, i.e. if the thickness of the casing is unchanged along the measured distance or the tool has stopped.

Each sensor 5, 6 measures the same changes, but there is a difference in time between the measurements due to the distance between the sensors. The data from the sensors 5, 6 is convoluted, and from the maximum value of the convolution, it can be deducted when a first sensor 5 passes the same position as a second sensor 6, and so forth. The period between the time where the first and the second sensor pass the same positions is named ΔT, and since the distance $d_2$ between the first 5 and the second sensor 6 is known, it is possible to calculate the velocity of the positioning tool 1 by means of the following equation:

$$v_{estimate} = \frac{d_2}{\Delta T}$$

The estimate of the velocity is based on a number of measurements, and by continuously calculating the velocity of the tool 1, it is possible to calculate the distance Δx travelled since the previous calculation by means of the following equation:

$$\Delta x = v \cdot \Delta t$$

where Δt is the time between calculations and Δx is the estimated velocity. When adding these estimated distances, the distance from the top of the well at a specific time of e.g. an observation of an irregularity, such as a leak, is known.

Using convolution between datasets received from at least two sensors instead of only comparing the measurements from one sensor with measurements from the other measurement by measurement, the method is relatively insensitive to noise in the measurements. In this way, a more accurate result is obtained. Furthermore, since the same characteristics are present in the two sets, the scale of the data is not important.

When the tool 1 passes a joint or collar where two casing parts are mounted together, the change in field direction is substantially increased. At this point, the distance from a collar is zero, and any errors in the estimated position of the tool can be eliminated. The number of past collars and the distance from the last collar indicate the actual position of the tool since the distance between collars is known.

If a change in field direction between two collars is substantially increased, this must be caused by another feature, and based on the knowledge of the completion or the extent of the feature, the type of feature, such as a valve, a patch, a leak etc., can be determined.

Figure 2:
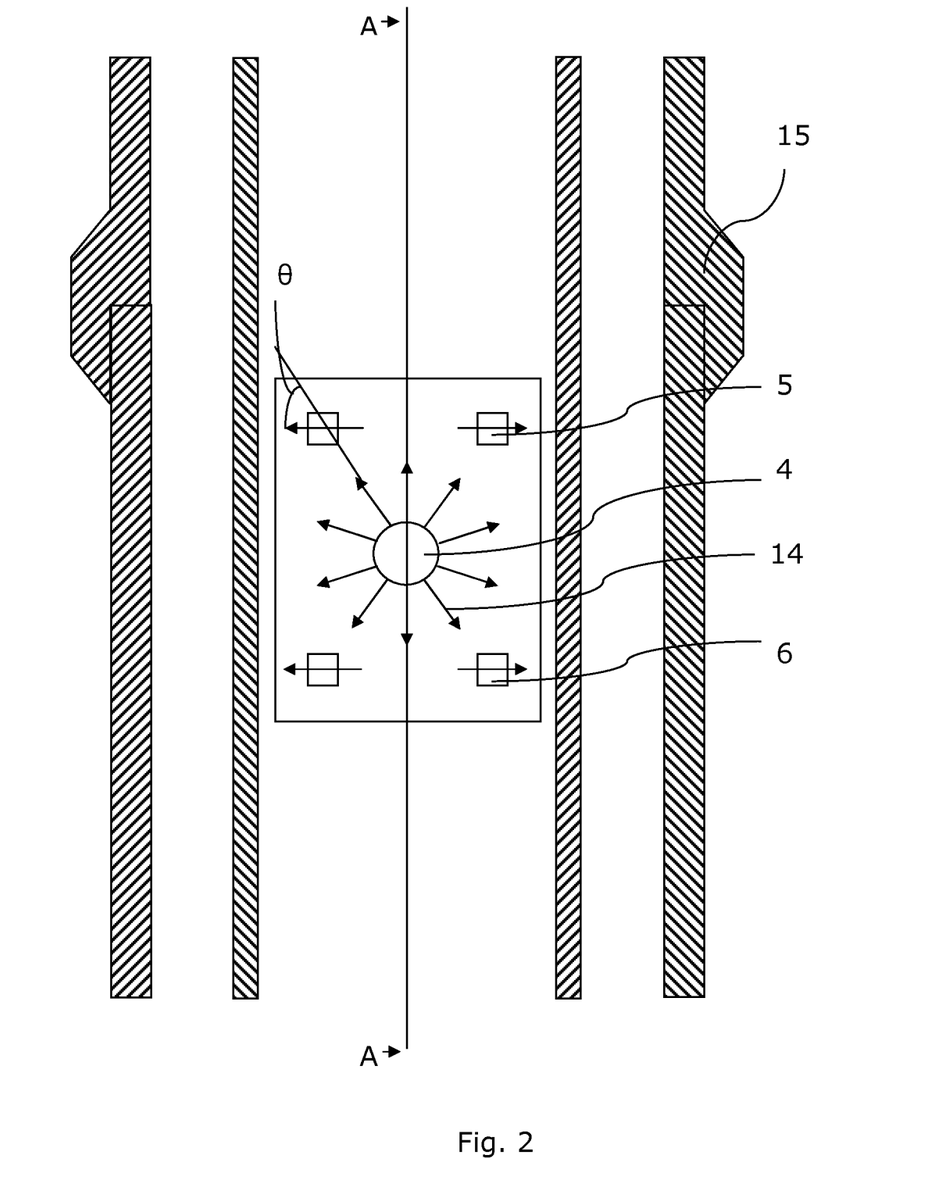
FIG. 2 shows another embodiment of the tool.

The detecting unit 2 of FIG. 2 only has four sensors 5, 6, and only two of the sensors arranged on the same side of the magnet 4 are necessary to calculate the position of the tool. The closer the two sensors 5, 6 are arranged in the longitudinal direction of the tool, the faster the measurements can be processed.

Figure 3:
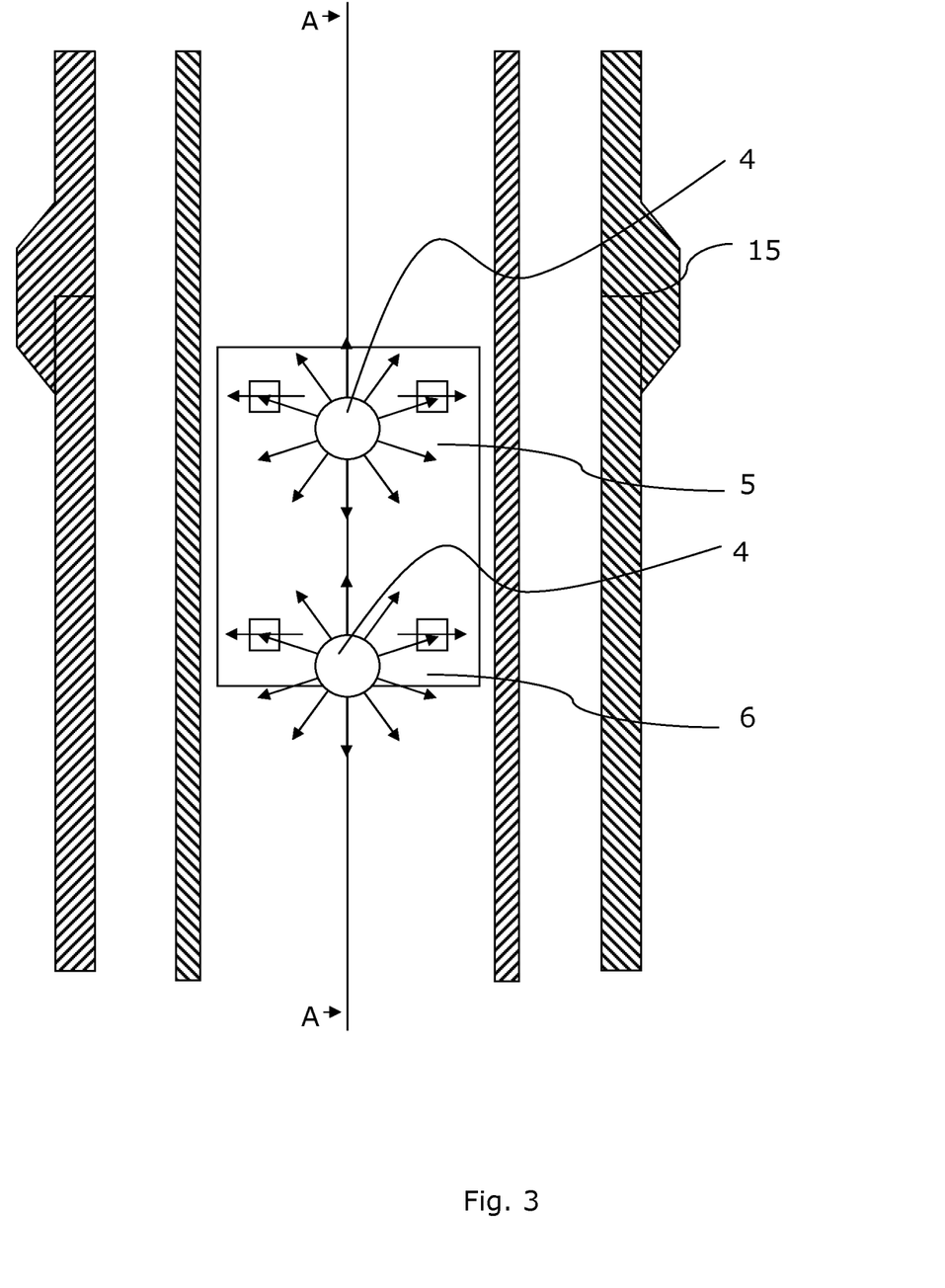
FIG. 3 shows yet another embodiment of the tool.

As it appears from FIGS. 3 and 4, one magnet 4 can be arranged outside a sensor 5, 6 so that the first magnet is arranged outside the first sensor and the second magnet is arranged outside the second sensor. When there is a magnet 4 outside each sensor 5, 6, all sensors are positioned with the same distance to the magnet, which results in a more precise measurement, again resulting in a better velocity estimates.

The magnet/magnets 4 can be positioned on a plate 8, such as a circuit board. As it appears in the cross-sectional view of FIG. 5, a magnet 4 may be arranged on the other side of the plate 8 to direct the magnetic field lines along the extension of the plate and thereby in the direction of the sensors 5, 6. In FIGS. 1, 2, 3 and 5, the magnet 4 has a cylindrical shape, and as it appears in FIG. 5, repelling poles, such as the south poles of the two opposing magnets, face one another. However, it could also be the north poles.

The magnet 4 is surrounded by a housing 16 of non-magnetic material in order to hold them in place. The non-magnetic material may be any type of substantially non-magnetic material, such as aluminum, porcelain, ceramic, mica, glass, plastics or a combination thereof.

The plate 8 may be any type of plane substance, and it may be made of any suitable non-magnetic material, such as aluminum, porcelain, ceramic, mica, glass, plastics or a combination thereof.

In FIG. 4, magnets 4 are only arranged on one side of the plate 8. Each magnet 4 has a pole facing one sensor 5, 6, and the repelling poles face the other sensor. In this way, the field lines extend into the sensor 5, 6 without a second magnet 4 on the other side of the plate 8 being needed to direct the lines.

The distance between the sensors 5, 6 does not have to be the same, and the distance between the first two sensors in a row of four may therefore be different than the distance between the second and third or the third and fourth sensors.

The distance $d_1$ from a sensor to the magnet is the distance from the longitudinal axis of the detecting unit on which the centre of the magnet is arranged as shown in FIG. 1.

Figure 4A:
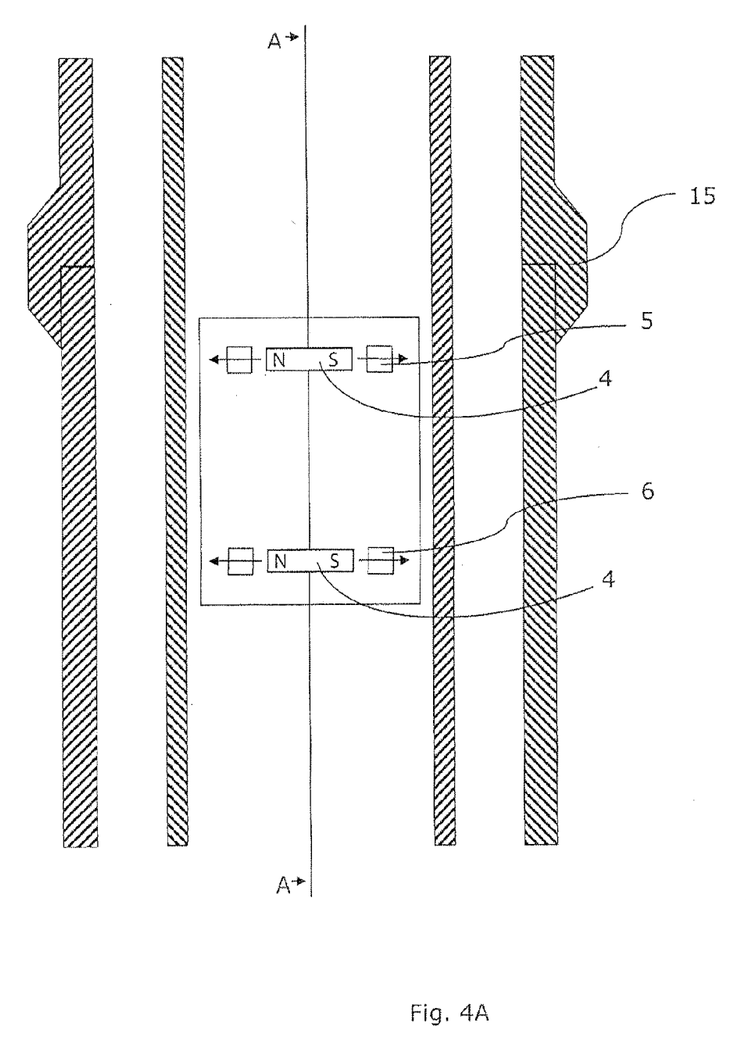
FIG. 4A shows yet another embodiment of the tool.
Figure 4B:
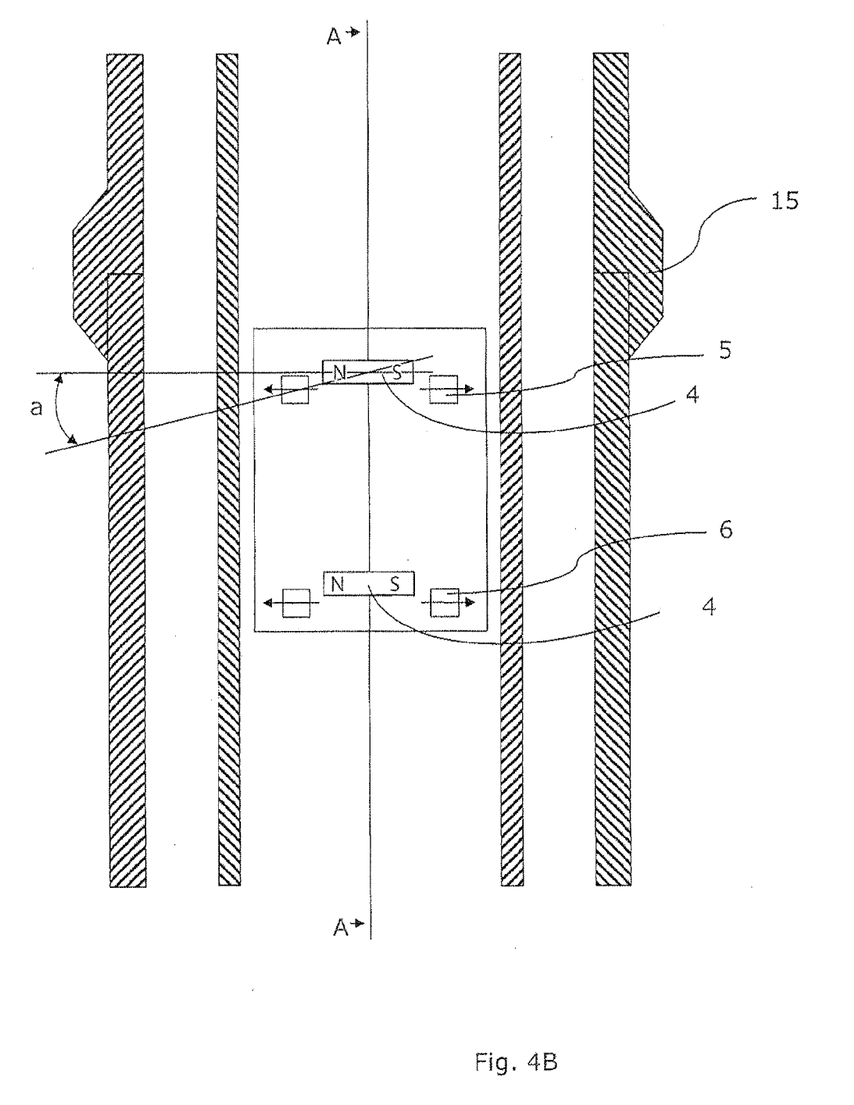
FIG. 4B shows yet another embodiment of the tool.
Figure 5:
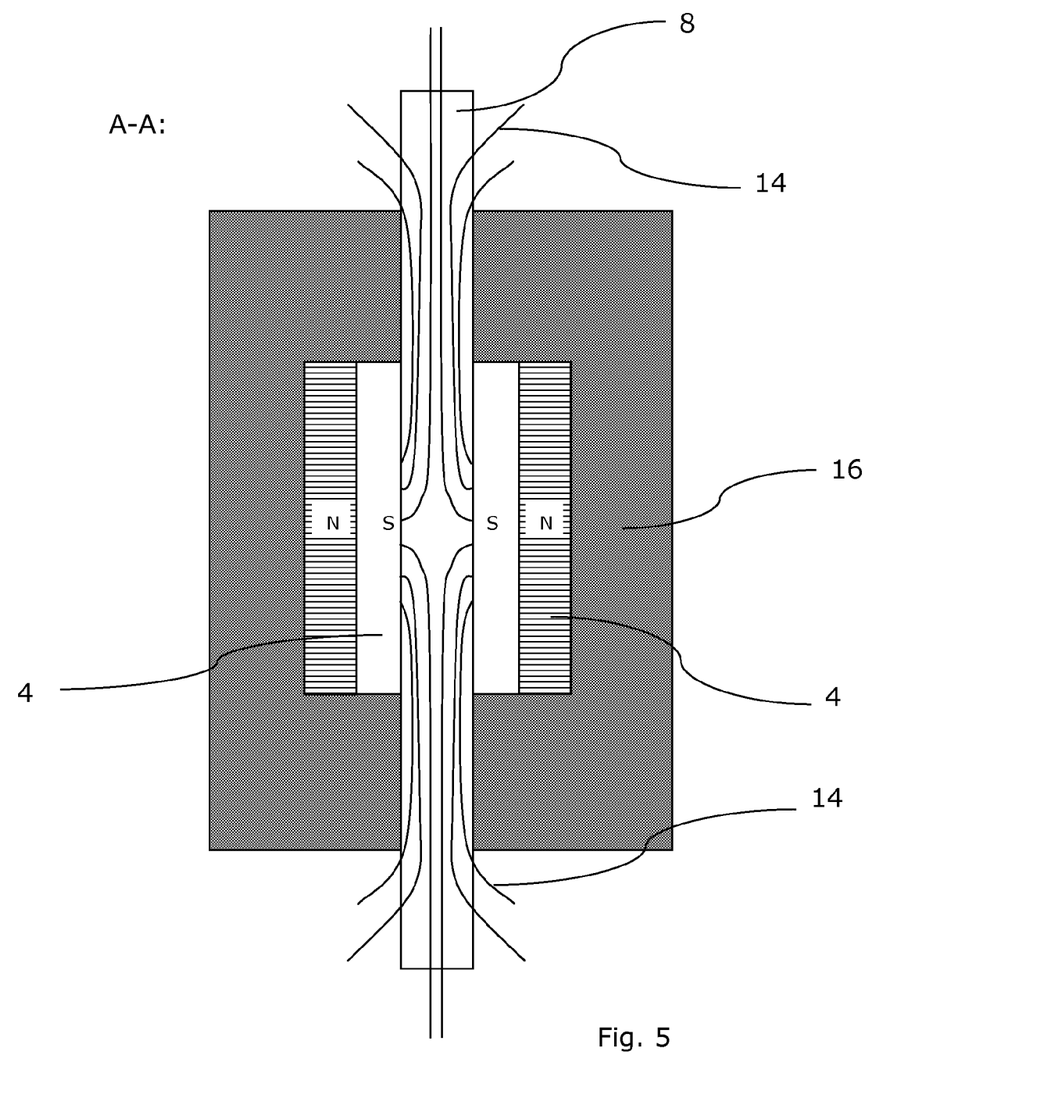
FIG. 5 shows a cross-sectional view of a magnet.

As shown in FIGS. 3, 4A and 4B, the sensors are arranged in the same position relative to the magnets 4 so that a sensor and a magnet are arranged in a pair and so that two adjacent pairs are placed in the same plane, only separated by a distance along the longitudinal axis of the detecting unit 2. This setup is employed to achieve the best quality signals. If the sensors were not placed in the same position relative to their corresponding magnet, the signals obtained from the sensors would be less similar and thereby cause errors and inaccuracies in the results of the processing of the measurements.

FIG. 4B shows another example of how the sensors might be placed in relation to the magnets while still meeting the criteria for good signal quality described above. The sensors are displaced relative to the corresponding magnet along the longitudinal axis of the tool. As can be seen in FIG. 4B in relation to FIG. 4A, the sensors 5, 6 may be arranged with an angle a in relation to the longitudinal extension of the magnet 4. The longitudinal extension of the magnet 4 is transverse to the longitudinal extension of the tool 1. In FIG. 4A, the angle a is zero as the sensors 5, 6 are arranged on a centre axis coincident with the longitudinal extension of the magnet 4.

The sensors 5, 6 may be arranged in different positions relative to the magnetic sources, as shown in FIGS. 1 and 2. However, as mentioned above, the signals obtained from this setup are less useful for the described method as they will be less similar. This will either cause errors in the results or require complex compensation of the signals prior to their processing.

The sensors 5, 6 detect the direction and/or the magnitude of the magnetic field, and the magnet 4 has a magnetic field source axis substantially transverse to the longitudinal tool axis, as shown in FIG. 4B.

Figure 6:
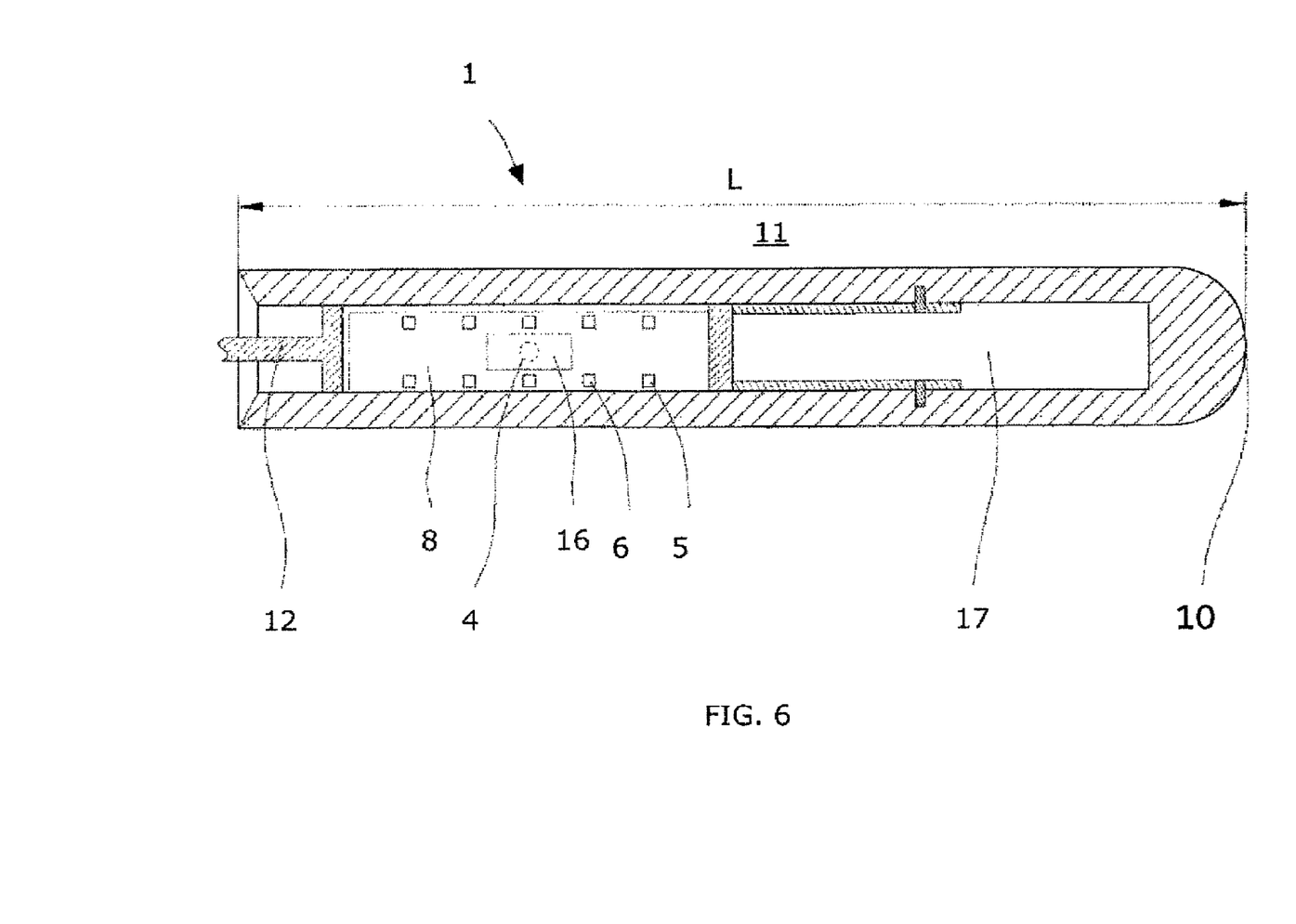
FIG. 6 shows a cross-sectional view of the tip of an embodiment of the tool.

A partly cross-sectional view of the positioning tool 1 is shown in FIG. 6. The detecting unit 2 is arranged at a distance from the tip 10, which is approximately half the length L of the positioning tool. There is a space 17 in front of the detecting unit for mounting any other logging or measuring device which can make observations downhole. The detecting unit 2 provides the measurements for determining the position of each of the observations made by the logging or measuring device.

Figure 7:
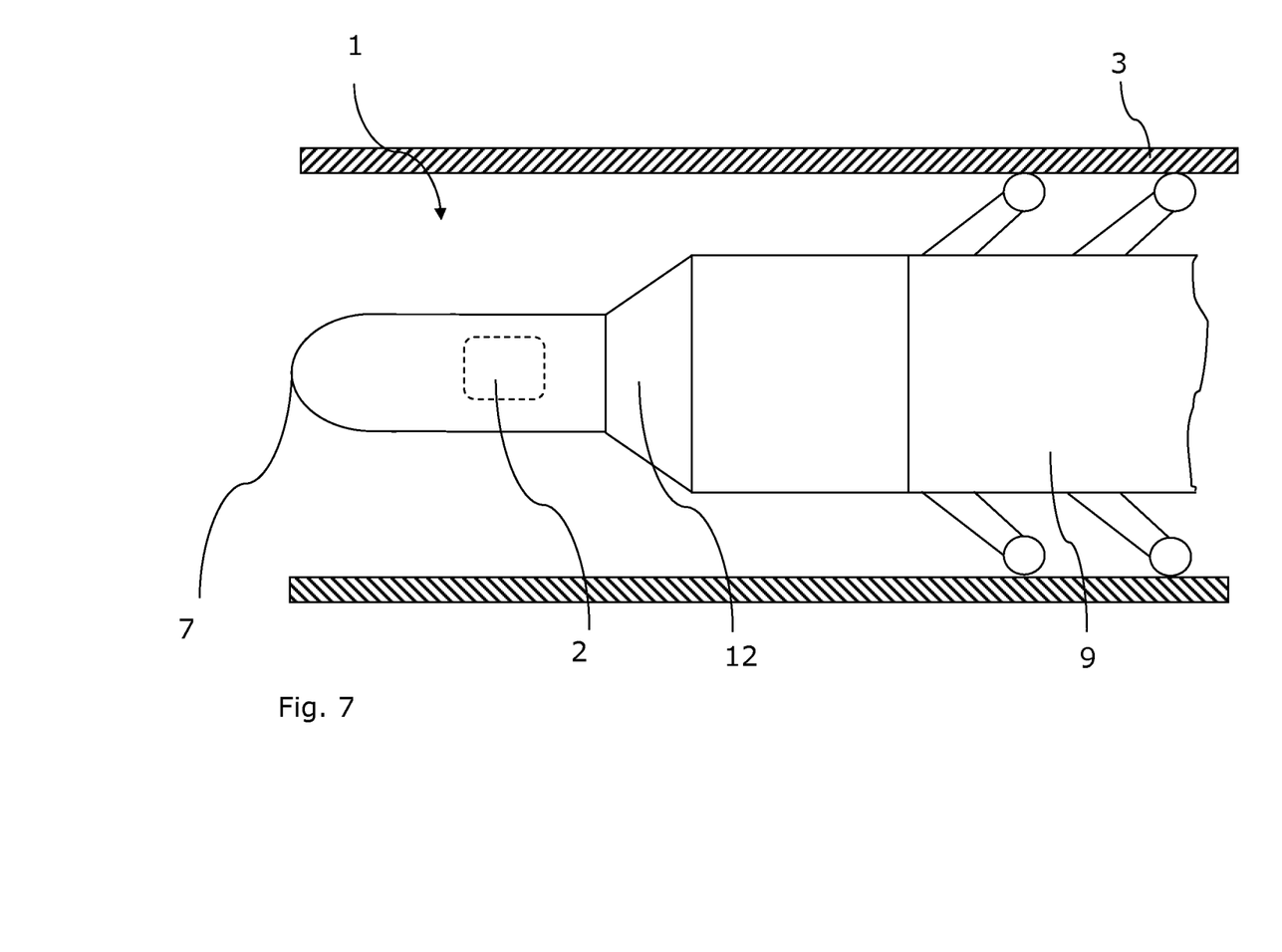
FIG. 7 shows a positioning tool in connection with a driving unit.

In another embodiment, the detecting unit is positioned elsewhere in the tool, as shown in FIG. 7.

FIG. 7 shows a positioning tool 1 having a tip 10 and a longitudinal extension stretching from the tip towards the driving unit 9. As can be seen, the positioning tool 1 is surrounded by well fluid 11, and the detecting unit 2 is situated in the front of the tool. The positioning tool 1 is connected with the driving unit 9 in a connection joint 12.

As mentioned above, the positioning tool 1 may be connected with a driving unit 9, such as a downhole tractor, as shown in FIG. 7. When e.g. a leak is detected by another tool, the positioning tool 1 may identify the position of the leak. Subsequently, the leak can be repaired by another tool section in the same tool or by another tool in a second run.

The magnets 4 may be permanent magnets, electromagnets or any other suitable type of magnets. By using permanent magnets 4, no extra equipment is needed in order for the magnet to function.

Figure 8:
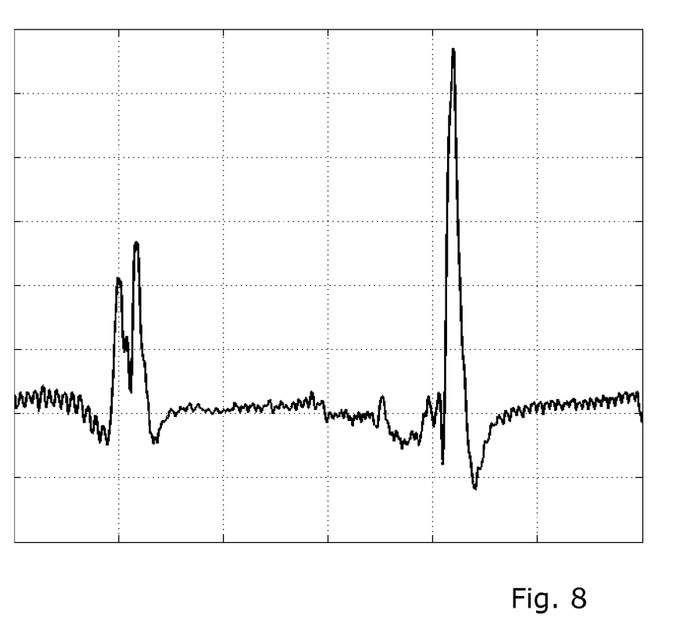
FIG. 8 shows a graph of measurements obtained while the positioning tool passes two casing collars.

In FIG. 8, a graph of the measurements from one sensor is shown. As can be seen, the graph has two peaks, each representing the point where the sensor passes a casing collar.

Figure 9:
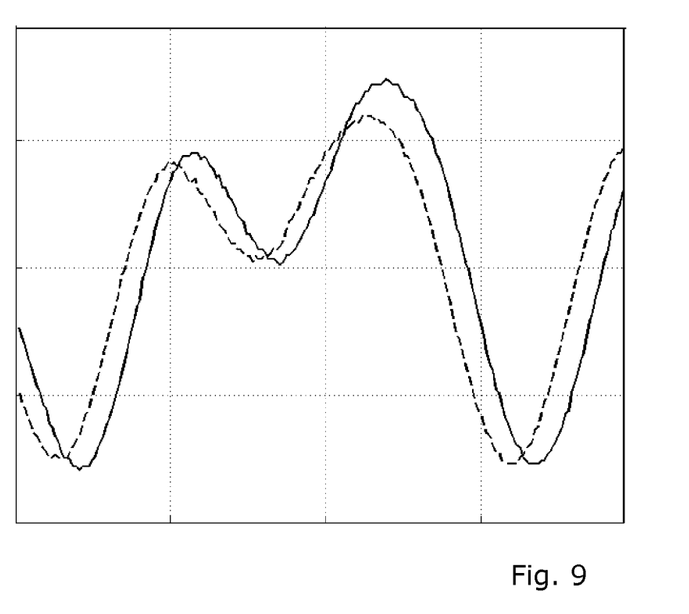
FIG. 9 shows a graph of measurements from two sensors.

The distance between the sensors 5, 6 may vary according to design. In FIG. 9, a graph of the measurements made by the two sensors 5, 6 is shown. The horizontal distance between the curves is a measure of the current velocity of the tool 1. As can be seen, the two sensors 5, 6 detect the same changes in the magnetic field when passing the same position.

If the sensors 5, 6 are placed with a long distance between them, the variations in tractor speed may be missed or at least not detected instantaneously. In one embodiment, the distance between the two sensors 5, 6 is between 5 and 150 mm, preferably between 5 and 100 mm, more preferably between 10 and 50 mm, and even more preferably between 10 and 30 mm.

The sensors 5, 6 do not have to be arranged on a flat substance such as a plate 8. They may be positioned in individual plates or clamps as long as they are arranged in substantially the same plane.

The sensors 5, 6 conduct measurements at a sample rate between 1 and 5000 measurements per second, preferably between 100 and 2000 measurements per second and more preferably between 250 and 1000 measurements per second.

The calculation of the velocity of the tool 1 is based on between 1 and 300 times per second, preferably between 10 and 100 times per second and more preferably between 10 and 50 times per second.

The positioning tool 1 may comprise a calculation unit, such as a processor, for calculation of the velocity or the position of the tool.

The invention also relates to a system comprising a positioning tool 1 as described above and a calculation unit positioned at a distance from the tool, e.g. above surface on an oil rig or vessel. The tool itself may have a calculation unit, meaning that some of the calculations are performed downhole in order to reduce the amount of data transmitted to the calculation unit above surface.

The sensors 5, 6 may be any type of suitable magnetic sensors, such as an anisotropic magnetoresistive sensor, capable of measuring the direction of the magnetic field from a magnet 4. By direction sensitive sensor is meant a sensor capable of measuring the direction of the magnetic field surrounding the sensor such as from a magnet nearby. When the tool 1 has an anisotropic magnetoresistive sensor, the determination of the position of the tool is independent of the velocity of the tool. Many types of anisotropic magnetoresistive sensors are very commonly available and therefore inexpensive, without being less reliable.

The choice of magnet type depends on the temperature downhole.

When using several magnets 4 in the same plane, each magnet must have a certain distance to the adjacent magnets to ensure that the casing 3 and the casing collars 15 can influence the direction of the magnetic field generated by the individual magnet. The distance is preferably at least 5 mm, more preferably 5-50 mm, and even more preferably 10-30 mm.

Figure 10:
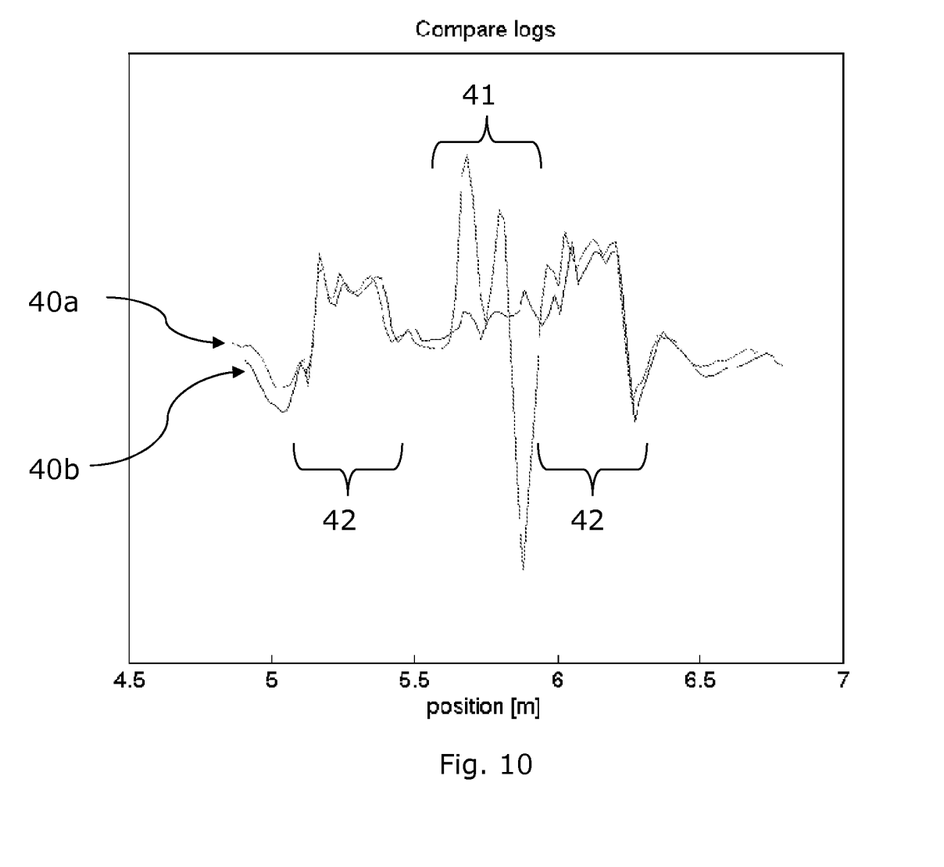
FIG. 10 shows a graph of measurements obtained before and after a sleeve has changed position.

The positioning tool 1 may also be used for verifying that a given operation has taken place. The positioning tool 1 is used for providing a profile of the casing 3 to verify if e.g. a sleeve has been moved as requested. In this case, the positioning tool 1 conducts a sequence of measurements when moving past the sleeve before the sleeve is moved, and when the sleeve has been moved, the positioning tool repeats its measurements. The sequences of measurements before and after the operation are then compared by drawing up the casing profiles on top of each other. An example of this is shown in FIG. 10 where a first casing profile 40*a* before manipulation of a sleeve is created and compared to a second casing profile 40*b* made after the manipulation. The middle part 41 containing the sliding sleeve is different, but the surrounding parts 42 showing joints or collars on either side of the sleeve are similar. This shows that the sleeve in the middle was moved.

Using the described technique of comparing profiles, a number of downhole operations may be readily confirmed, e.g. perforations, retrieving or setting plugs and valves. The positioning tool 1 may even be placed in the same tool string as the tools necessary for the given operation. Hence, the verification of the operation may be performed in the same run as the operation, allowing the well to start producing earlier.

By fluid or well fluid is meant any type of fluid that may be present in oil or gas wells, such as natural gas, oil, oil mud, crude oil, water etc. By gas is meant any type of gas composition present in a well, completion or open hole, and by oil is meant any type of oil composition, such as crude oil, an oil-containing fluid etc. Gas, oil and water fluids may therefore all comprise other elements or substances than gas, oil and/or water, respectively. The fluid may also be a combination of gas, oil, water and small solids in the fluid.

By a casing 3 is meant all types of pipes, tubings, tubulars etc. used downhole in relation to oil or natural gas production.

In the event that the tools are not submergible all the way into the casing 3, a downhole tractor can be used to push the tools all the way into position in the well. A downhole tractor is any type of driving tool capable of pushing or pulling tools in a well, such as a Well Tractor®.

Although the invention has been described in the above in connection with preferred embodiments of the invention, it will be evident for a person skilled in the art that several modifications are conceivable without departing from the invention as defined by the following claims.

The invention claimed is:

1. A positioning tool for determining a position in a casing downhole, the positioning tool having a longitudinal tool axis and comprising:
    a detecting unit comprising:
        a first magnet to generate a first magnetic field,
        a first sensor arranged in a first plane and at a first distance from the first magnet to detect changes in the magnetic field,
        a second magnet to generate a second magnetic field arranged in the first plane, the second magnet being arranged spaced from the first magnet in a direction parallel to the longitudinal tool axis at a magnet distance, the magnet distance being the distance between the first magnet and the second magnet; and
        a second sensor arranged in the first plane and at a second distance from the second magnet and the second sensor is arranged spaced from the first sensor in a direction parallel to the longitudinal tool axis at a sensor distance, the sensor distance being the distance between the first sensor and the second sensor, also to detect changes in the magnetic field;
    wherein the sensors are configured to detect changes in the magnitude and/or direction of the magnetic field, the first magnet and the second magnet having a magnetic field source axis substantially transverse to the longitudinal tool axis; and the second sensor is positioned in relation to the second magnet such that the second sensor is offset from the second magnet by substantially the same vector as the first sensor is offset from the first magnet.

2. A positioning tool according to claim 1, wherein the first sensor is positioned in a first angle in relation to a longitudinal extension of the first magnet, and the second sensor is positioned in the first angle in relation to a longitudinal extension of the second magnet.

3. A positioning tool according to claim 1, wherein the first and second sensors are arranged on one side of the first magnet and a plurality of sensors are arranged on the other side of the first magnet in the first plane.

4. A positioning tool according to claim 1, wherein the first magnet and the second magnet are arranged on one side of a longitudinal plate and a set of complementary magnets arranged on the other side of the plate such that a first pole of the first magnet and a first pole of a first complementary magnet are arranged to face one another, the first pole of the first magnet and the first pole of the first complementary magnet having the same polarity.

5. A positioning tool according to claim 1, wherein the tool comprises a plurality of magnets each of which is arranged outside a sensor.

6. A positioning tool according to claim 1, wherein the at least one magnet is a permanent magnet or an electromagnet.

7. A positioning tool according to claim 1, wherein each sensor measures the magnitude and/or direction of the magnetic field in that sensor.

8. A positioning tool according to claim 1, wherein the distance between two sensors is between 5 and 150 mm.

9. A method for determining a position of a tool based on the measurements derived from the positioning tool according to claim 1, comprising:
measuring the magnitude and/or direction of a magnetic field by means of the first sensor several times over a time period;
measuring the magnitude and/or direction of the magnetic field by means of the second sensor several times over a time period; and
comparing the measurements from the first sensor with the measurements from the second sensor in order to calculate a velocity of the tool.

10. A method according to claim 9, wherein the steps of measuring the magnitude and/or direction of the magnetic field are performed several times over a time period, and wherein the step of comparing the measurements from the sensor is performed after this time period.

11. A method according to claim 9, wherein the tool is moving during the measurements.

12. Use of the positioning tool according to claim 1 downhole or in a well.

13. A positioning system comprising:
the positioning tool according to claim 1; and
a calculation unit configured to process magnetic field data measured by the sensors.

14. A positioning system according to claim 1, wherein the distance between two sensors is between 5 and 100 mm.

15. A positioning system according to claim 1, wherein the distance between two sensors is between 10 and 50 mm.

16. A positioning system according to claim 1, wherein the distance between two sensors is between 10 and 30 mm.

17. A method according to claim 10, wherein the tool is moving during the measurements.

18. A positioning tool for determining a position in a casing downhole, the positioning tool having a longitudinal tool axis and comprising:
a detecting unit comprising:
a first magnet;
a second magnet arranged opposite the first magnet such that like poles face each other;
a first sensor;
a second sensor;
a plate located between the first magnet and the second magnet and arranged coaxially with the positioning tool along the longitudinal tool axis;
a first housing surrounding the first magnet except on a first face of the first magnet which abuts the plate; and
a second housing surrounding the second magnet except on a first face of the second magnet which abuts the plate;
wherein the first and the second magnet are arranged to direct their respective magnetic field lines along extensions of the plate and thereby in the direction of the first and second sensor.

19. The positioning tool according to claim 1, wherein the magnet distance further comprises a distance between the first magnet and the second magnet without any additional magnet therebetween.

20. The positioning tool according to claim 1, wherein the sensor distance further comprises a distance between the first sensor and the second sensor without any additional sensor therebetween.

* * * * *